(12) United States Patent
Braun et al.

(10) Patent No.: US 10,492,772 B2
(45) Date of Patent: Dec. 3, 2019

(54) RESECTION TOOLS AND RELATED METHODS OF USE

(71) Applicant: Boston Scientific Scimed, Inc., Maple Grove, MN (US)

(72) Inventors: Johnathan J. Braun, New Brighton, MN (US); Selina M. Merkling, St. Louis Park, MN (US); Kimberly Anne Robertson, Forest Lake, MN (US); Matthew Nelson Frost, Watertown, MN (US); Adam Huot, Maple Grove, MN (US); Daniel J. Gregorich, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 242 days.

(21) Appl. No.: 15/382,124

(22) Filed: Dec. 16, 2016

(65) Prior Publication Data

US 2017/0172684 A1 Jun. 22, 2017

Related U.S. Application Data

(60) Provisional application No. 62/269,556, filed on Dec. 18, 2015.

(51) Int. Cl.
| | | |
|---|---|---|
| A61B 17/02 | (2006.01) | |
| A61B 1/32 | (2006.01) | |
| A61B 17/3205 | (2006.01) | |
| A61B 1/00 | (2006.01) | |
| A61B 17/3207 | (2006.01) | |
| A61B 17/00 | (2006.01) | |
| A61B 17/32 | (2006.01) | |
| A61B 17/34 | (2006.01) | |

(52) U.S. Cl.
CPC ...... *A61B 17/0218* (2013.01); *A61B 1/00133* (2013.01); *A61B 1/00135* (2013.01); *A61B 1/32* (2013.01); *A61B 17/3205* (2013.01); *A61B 17/320758* (2013.01); *A61B 17/320783* (2013.01); *A61B 2017/00004* (2013.01); *A61B 2017/00269* (2013.01); *A61B 2017/00867* (2013.01); *A61B 2017/00876* (2013.01); *A61B 2017/32006* (2013.01); *A61B 2017/3452* (2013.01)

(58) Field of Classification Search
CPC ......... A61B 90/00; A61B 90/02; A61B 17/02; A61B 17/0218; A61B 17/0293
See application file for complete search history.

(56) References Cited

U.S. PATENT DOCUMENTS

| | | |
|---|---|---|
| 8,506,479 B2 | 8/2013 | Piskun et al. |
| 2004/0210116 A1 | 10/2004 | Nakao |
| 2012/0095498 A1 | 4/2012 | Stefanchik et al. |
| 2013/0110109 A1 | 5/2013 | Nguyen et al. |
| 2014/0012192 A1* | 1/2014 | Bar-On ............ A61F 2/04 604/93.01 |
| 2014/0379012 A1* | 12/2014 | McRae ............ A61M 25/007 606/159 |
| 2015/0045616 A1 | 2/2015 | Piskun |

* cited by examiner

*Primary Examiner* — Christopher J Beccia
(74) *Attorney, Agent, or Firm* — Bookoff McAndrews, PLLC

(57) ABSTRACT

A device for treating tissue may include a tissue expander configured to be inserted into a body lumen and stretch tissue surrounding the body lumen, and a tool configured to be coupled to the tissue expander and move along a path defined by the tissue expander.

20 Claims, 8 Drawing Sheets

RESECTION TOOLS AND RELATED METHODS OF USE

CROSS-REFERENCE TO RELATED APPLICATION(S)

This patent application claims the benefit under 35 U.S.C. § 119 to U.S. Provisional Patent Application No. 62/269,556, filed on Dec. 18, 2015, the entirety of which is incorporated herein by reference.

TECHNICAL FIELD

Examples of the present disclosure relate to resection tools and related methods of use.

BACKGROUND

Colorectal cancer is a leading cause of death in the United States. One treatment option for the removal of malignant and pre-malignant lesions is endoscopic mucosal or en bloc resection. Resections can allow for the pathological determination of tissue health.

In order to remove the tissue, the surgeon often carefully cuts through the mucosa and submucosa, a process which is time consuming and difficult as the tissue easily deforms and deflects when pressure is applied. Other challenges include difficulty in locating the submucosal layer, maintaining an adequate lift height for a duration long enough to perform the resection, difficulty injecting the lifting solution through conventional injection needles, and repeatedly exchanging devices through an endoscope.

SUMMARY

In one aspect, the present disclosure is directed to a medical device. The device may include a tissue expander configured to be inserted into a body lumen and lift tissue surrounding the body lumen, and a tool configured to be coupled to the tissue expander and move along a path defined by the tissue expander.

The tissue expander may include a first support ring and a second support ring, wherein the path may be defined at a first end by the first support ring and at a second end by the second support ring, and wherein the tool may be configured to move circumferentially along the path. The device may include one or more spacers disposed between the first support ring and the second support ring, wherein the one or more spacers may be longitudinally expandable. The tool may include a first attachment portion configured to be coupled to the first support ring, and a second attachment portion configured to be coupled to the second support ring, wherein a length of the tool between the first attachment portion and the second attachment portion may be equal to a length of the one or more spacers. The first attachment portion may include a first mating feature, the second attachment portion may include a first mating feature, the first support ring may include a second mating feature disposed on at least one of a proximally-facing surface and a distally-facing surface, and the second support ring may include a second mating feature disposed on at least one of a proximally-facing surface and a distally-facing surface, wherein the first mating feature of the first attachment portion may be complementary to the second mating feature of the first support ring, and wherein the first mating feature of the second attachment portion may be complementary to the second mating feature of the second support ring. One of the first mating feature and the second mating feature may be a recess, and the other of the first mating feature and the second mating feature may be a pin, bearing, ball, protrusion, wheel, or roller configured to be received by the recess. The tool may include a cutting member extending radially outward when the tool is coupled to the tissue expander. The tissue expander may include anchoring features extending radially outward from an outer circumferential surface.

In another aspect, the present disclosure is directed to a medical device. The device may include a first support, and a plurality of leg assemblies coupled to the first support, wherein the plurality of leg assemblies may be circumferentially arranged about a central longitudinal axis of the device, wherein at least one pair of adjacent leg assemblies may be separated from one another by a first angle defined in a plane that is normal to the central longitudinal axis of the device, and wherein remaining pairs of adjacent leg assemblies may be separated from one another by second angles defined in the plane that are less than the first angle. Each of the plurality of leg assemblies may include a first pivot joint connecting a corresponding leg assembly to the first support; a first leg extending from the first pivot joint, the first leg being configured to pivot relative to the first support via the first pivot joint, a second pivot joint disposed at a distal end of the first leg, and a second leg extending distally from the second pivot joint, the second leg being configured to pivot relative to the first leg via the second pivot joint.

Distal ends of each of the second legs may be unconnected to one another, the first angle may be from 80 degrees to 120 degrees, and each of the second angles may be from 20 degrees to 60 degrees. The first leg and the second leg of each of the plurality of leg assemblies may be substantially parallel to the central longitudinal axis when the device is in a collapsed configuration. The device may be movable to an expanded configuration, wherein in the expanded configuration, the first leg of each of the plurality of leg assemblies may be transverse to the central longitudinal axis, and the second leg of each of the plurality of leg assemblies may be substantially parallel to the central longitudinal axis. The device may further include a second support disposed proximally of the first support, and a plurality of linkages extending from the second support, wherein at least one linkage of the plurality of linkages may be coupled to each first leg of the plurality of leg assemblies, wherein, when a proximal force is applied to the second support, the second support may move proximally relative to the first support to cause the linkages to pull proximally on each first leg of the plurality of leg assemblies, causing each first leg to pivot proximally via its respective first pivot joint, and moving the device to the expanded configuration. The first support and the second support ring each may include a lumen, and wherein the lumens of the first support and the second support may be aligned to enable the passage of an endoscope through the lumens. Each first pivot joint may include a locking mechanism configured to limit a proximal retraction of a respective first leg.

In yet another aspect, the present disclosure is directed to a method of manipulating tissue. The method may include stretching tissue with a tissue expander to define body lumen, positioning a tool relative to the tissue expander, and moving the tool along a path defined by the tissue expander.

The tissue expander may include a first support ring and a second support ring, wherein the path defined by the tissue expander may be a circumferential path defined at a first end by the first support ring, and at a second end by the second support ring. The method may include, before the using step, positioning the second support ring distal to a targeted treatment area, and positioning the first support ring proximal to the targeted treatment area, wherein the stretched tissue may include the targeted treatment area disposed between the first support ring and the second support ring. The tool may include a cutting member, and moving the tool along the path defined by the tissue expander may remove a portion of the stretched tissue defining the body lumen. The body lumen may be located within a colon.

BRIEF DESCRIPTION OF THE DRAWINGS

The accompanying drawings, which are incorporated in and constitute a part of this specification, illustrate various examples and together with the description, serve to explain the principles of the disclosed examples.

DETAILED DESCRIPTION

Reference will now be made in detail to examples of the present disclosure, which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

In at least some examples, the present disclosure is directed to systems, devices, and methods used to facilitate endomucosal or en bloc resection of colorectal or other tissues. Some components of the system may be used to stretch and hold tissue walls (e.g., the colorectal wall) in a regular cylindrical shape or other suitable shape for resection of tissue. Other components of the system may help perform the actual resection by slicing and/or removing tissue.

Figure 1:
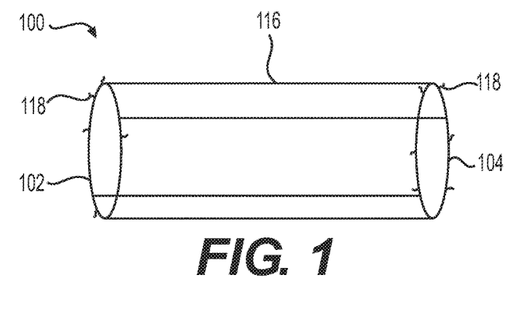
FIG. 1 is a side view of a tissue expander according to an example of the present disclosure.

A tissue expander 100 is shown in FIG. 1 in an expanded configuration. The tissue expander 100 may include a first support 102 and a second support 104. First support 102 may be a circular ring in one example, although first support 102 may include other suitable cross-sectional configurations such as, e.g., ovular, rectangular, or the like. First support 102 may be formed of any suitable biocompatible material such as, e.g., metals, alloys, plastics, or the like. The first support 102 may be biased toward the expanded configuration such that when a constraining force is removed from the first support 102, the first support 102 urges itself toward the expanded configuration. Thus, in some examples, first support 102 may be formed of a shape memory material such as, e.g., nitinol, that is set or pre-shaped into the expanded configuration. The first support 102 also may radially expand by another suitable mechanism, such as, e.g., by a ratcheting mechanism. For example the supports 102 and 104 could be linear pieces of metal. One end of each support 102, 104, may have ratcheting teeth or slots cut into it that slide into a receiver on the other end, thus forming a circular ring. The ring could then be expanded by or collapsed by actuating the teeth through the receiver. Actuation could be achieved by a micro-mechanism (e.g., similar to a hose clamp). For example, by actuating a screw in the receiver, the toothed or slotted end may be fed through the receiver. In another example, the device could be designed such that the operator may use a direct force on the inside diameter of the ring to open the ring, which may remain in a locked state until a release is activated on the receiver, at which point the ring may collapse due to the natural elasticity of the lumen being treated. In the expanded configuration, first support 102 may have any suitable diameter, such as, e.g., 0.1 mm to 50 mm, although other suitable sizes are also contemplated. In some examples, a balloon may be used to inflate the first support 102 and the second support 104. In other examples, more than two support rings are also contemplated.

Figure 2:
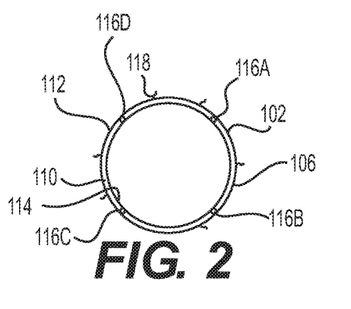
FIG. 2 is an end view of the tissue expander of FIG. 1.
Figure 6:
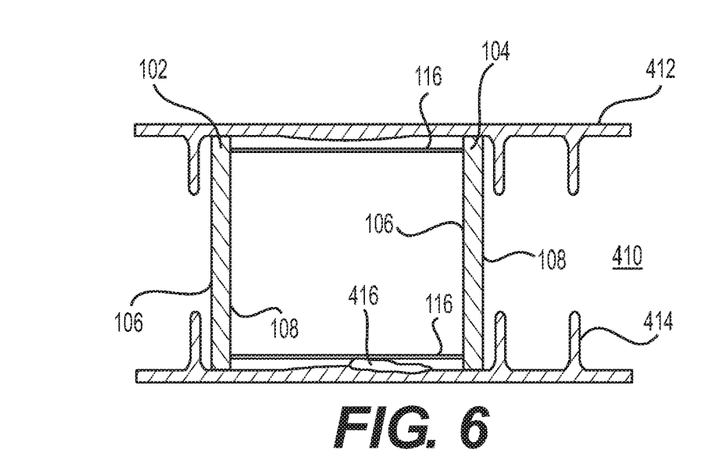

Referring to FIGS. 2 and 6, first support 102 may include a proximally-facing surface 106 and a distally-facing surface 108 (shown only in FIG. 6). One or more of the proximally-facing surface 106 and the distally-facing surface 108 may include mating features 110 configured to interface with corresponding mating features 312 disposed on a removal tool 300 as set forth in further detail below. In one example, the mating features 110 may include a recessed track configured to receive a protrusion, projection, roller, pin, ball, wheel, or other suitable element that may ride within the track. The mating features 110 may extend around an entirety of the proximally-facing surface 106 and the distally-facing surface 108 to enable the corresponding mating features 312 to translate around an entire circumference of an expanded body lumen. In another example, mating feature 110 may be a rail extending around the entirety of proximally-facing surface 106 and/or distally-facing surface 108. In some examples, mating features 110 and/or other portions of first support 102 may be magnetic, and may be magnetically attracted to the corresponding mating features 312.

Second support 104 may be substantially similar to first support 102, or may include one or more different features. First support 102 and second support 104 may be arranged such that only proximally-facing surface 106 of first support 102 includes mating features 110, while only the distally-facing surface 108 of second support 104 includes mating features 110. In other examples, the proximal-facing surface 106 and the distally-facing surface 108 of both first support 102 and second support 104 may include mating features 110.

Referring to FIG. 2, first support 102 and second support 104 each may include an outer circumferential surface 112 and an inner circumferential surface 114. Outer circumferential surface 112 may be disposed further from a radial center or a central longitudinal axis of first support 102 or second support 104 than inner circumferential surface 114. In some examples, the outer circumferential surface 112 may be the tissue-contacting surface of first support 102 or second support 104. The outer circumferential surface 112 may be roughened, notched, slotted, etched, sand-blasted, coated or otherwise modified to provide a better gripping surface and attachment to tissue walls surrounding a body lumen. In certain examples, inner circumferential surface 114 may be directly coupled to one or more spacers 116 as set forth in further detail below.

One or more spacers 116 may be disposed between first support 102 and second support 104. The spacers 116 may extend longitudinally between the first support 102 and the second support 104. The spacers 116 may be formed of a shape memory material that it is set or pre-shaped into a straight and linear expanded configuration as shown in FIGS. 1 and 6. Each spacer 116 disposed between first support 102 and second support 104 may be the same length, or may have slightly different lengths than one another. In some examples, the spacers 116 may be removable from the first support 102 and the second support 104. As alluded to above, the spacers 116 may be directly coupled to the inner circumferential surface 114 of the first support 102 and second support 104 such that mating feature 110 on the proximally-facing surface 106 or distally-facing surface 108 of the first support 102 and the second support 104 may not be interrupted by the spacers 116.

In another example, spacers 116 may not be formed from a shape memory material, but may instead be formed of a different biocompatible material. For example, spacers 116 may be stiff and linear linkages. In another example, spacers 116 may be manually actuated by a screw mechanism or other similar mechanical mechanism to achieve a desired distance between first support 102 and second support 104 in vivo. In one example, each spacer 116 and only one of the supports 102 or 104 may be threaded. The non-threaded support may be fixed to each spacer in such a way that the spacer is allowed to rotate but not travel longitudinally. In the initial configuration, each spacer may extend beyond the threaded support. By actuating the spacer clockwise or counter-clockwise, the threaded support may travel longitudinally along the spacer until a limit is reached. In another example, each support may have spacer that connect to a hub. The two hubs may be threaded with opposite twists and connected by a single threaded actuator with a matching twist on each half. When the actuator is rotated clockwise or counter-clockwise, the hubs may move closer together or father apart, forcing the supports connected by the spacers to move accordingly until a limit is reached. The spacing could be manually actuated or could be actuated by a piezoelectric motor or array of motors controlled by an ex vivo driver. In another example, the distance between the support rings may be controlled by a zip-tie.

Spacers 116 may be attached to first support 102 and second support 104 at circumferentially spaced locations to enable a removal tool 300 (described below) to translate along a circumferential path disposed between adjacent spacers 116. The spacers 116 may be biased longitudinally outwardly to cause first support 102 and second support 104 to separate. In the example shown in FIGS. 1 and 2, tissue expander 100 includes four spacers 116 equally spaced apart from one another at approximately 90 degree intervals, although other suitable configurations are also contemplated. For example, another suitable number of spacers 116 may be utilized to ensure the proper spacing between the first support 102 and the second support 104. In other examples, spacers 116 may be positioned at uneven intervals. For example, while four spacers 116*a-d* are shown in FIG. 2, one or more of those spacers 116 may not be utilized.

In one example, only two spacers (e.g., spacers 116*a* and 116*c*) spaced approximately 180 degrees from one another may be used. In another example, spacer 116*d* may be omitted such that three spacers 116*a-c* are utilized. In this example, two pairs of adjacent spacers (e.g., spacers 116*a*-116*b* and 116*b*-116*c*) may be spaced approximately 90 degrees from one another, while another pair of adjacent spacers (e.g., spacers 116*a*-116*c*) may be spaced 180 degrees from one another.

Spacers 116 may also include an undulating shape to allow for lengthening and/or compression to change the distance between two support rings and to increase the scaffolding area. The spacers 116 may also have a configuration in which they bow in or out, exposing a larger surface area and/or offering additional support between the support rings.

Referring to FIGS. 1 and 2, first support 102 and second support 104 each may include anchoring features 118 configured to maintain the relative positions of the first support 102 and second support 104 after one, multiple, or all spacers 116 are removed from tissue expander 100 in vivo. Anchoring features 118 may extend radially outward from the outer circumferential surface 112. In some examples, the anchoring features 118 may be selectively deployable, removable, and bioabsorbable. That is, during insertion of tissue expander 100, the anchoring features 118 may not be in an active configuration such that the tissue expander 100 may be manipulated in vivo without excessive trauma to tissue. The anchoring features 118 then may be deployed into the tissue by any suitable mechanism, including, e.g., by manipulating one or more latches, switches, or ratchets. Once a resection procedure is completed, the anchoring features 118 may be disengaged from first support 102 and second support 104 by, e.g., a frangible link, so that first support 102 and second support 104 can be removed without excessive trauma to colorectal tissue. The anchoring features 118 may remain in the body once the operation is completed, where they may be absorbed and degraded in vivo over time. The bioabsorbable material may include one or more of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly (a-hydroxy acid), collagen or other connective proteins or natural materials, polycaprolactone, and copolymers of these materials as well as composites thereof and combinations of other biodegradable polymers.

Figure 3:
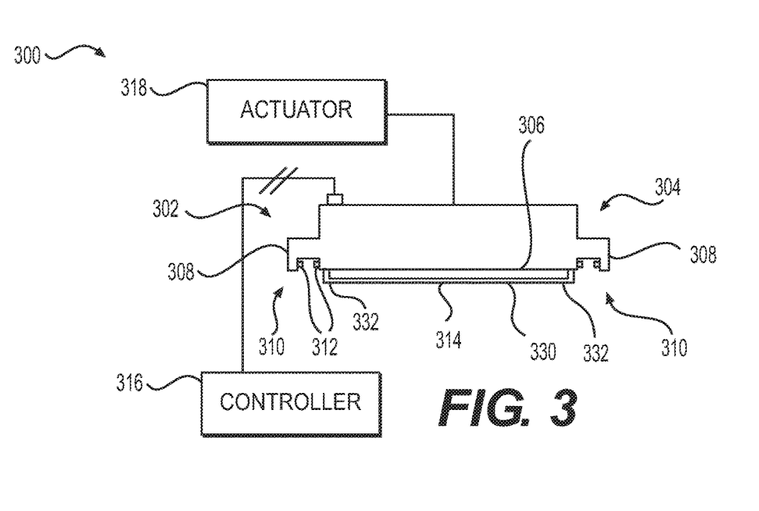
FIG. 3 is a schematic view of a removal tool according to an example of the present disclosure.

A removal tool 300 is shown in FIG. 3. Removal tool 300 may extend from a proximal end 302 to a distal end 304. A side surface 306 may extend between proximal end 302 and distal end 304. The proximal end 302 and distal end 304 each may include an attachment portion 308 configured to interface with and couple to first support 102 and second support 104 described above. The length of removal tool 300 between attachment portions 308 may be substantially the same as the length of spacers 116. The attachment portions 308 may include recesses 310 disposed within side surface 306. Mating features 312 may extend longitudinally toward one another and into recess 310 from opposing ends of the attachment portion 308, and may correspond to the mating features 110 disposed on the proximally-facing surface 106 and the distally-facing surface 108 of the support 102 and the second support 104. Mating features 312 may be protrusions, rollers, wheels, bearings or other suitable members that may ride along a rail or track provided by the mating features 110 of first support 102 and the second support 104.

In some examples, mating features 312 may be magnetic, and may be magnetically attracted to one or more portions of first support 102 and second support 104, such as, e.g., mating features 110.

Tool 300 also may include a cutting member 314 that extends radially outward from side surface 306. The cutting member 314 may be any suitable surgical cutting tool, such as, e.g., a knife, blade, edge, or the like. Cutting member 314 may include one or more other geometric features such as, e.g., serrations, teeth, tapers, bevels or the like to further facilitate spearing, cutting, or slicing of cutting member 314 through tissue. Cutting member 314 may have a cutting surface 330 that extends from side surface 306 at a first end 332 and at a second end 334. At least a portion of the cutting surface 330 may be spaced apart from the side surface 306. In the example shown in FIG. 3, cutting surface 330 is spaced from side surface 306 between first end 332 and second end 334. In other examples, cutting member 314 may be an electrosurgical cutting tool, or may include other suitable energy modalities such as, e.g., laser or high intensity focused ultrasound (HIFU).

Removal tool 300 may be coupled to a controller 316, which may include a processor that is generally configured to accept information from the system and system components, and process the information according to various algorithms to produce control signals for controlling cutting member 314. The processor may accept information from the system and system components, including various temperature, impedance, or other sensors, and process the information according to various algorithms. The processor may be a digital IC processor, analog processor, or any other suitable logic or control system that carries out the control algorithms. Controller 316 may include or may be otherwise coupled to a suitable power source (e.g., RF, laser, HIFU). Controller 316 also may be configured to control the degree to which cutting member 314 extends from side surface 306, or may otherwise control the depth of tissue through which cutting member 314 may penetrate. In some examples, the depth of cutting member 314 may be controlled manually.

Removal tool 300 may be coupled to an actuator 318 configured to move the removal tool 300 along a circumferential path around a body lumen, using first support 102 and/or second support 104 as guides. Actuator 318 may be any suitable mechanism, and may include mechanical linkages manually operated by a user, or may include a motor operated by a controller, such as, e.g., controller 316. Actuator 318 may be configured to move removal tool 300 in a first circumferential direction and a second circumferential direction that opposes the first circumferential direction. In one example, the operator could control the removal tool 300 by use of the endoscope and there may be no actuator 318 present. Actuator 318 may also be an array of piezoelectric motors that interface with the support rings 102 and 104 and are driven ex vivo by a controller.

Figure 4:
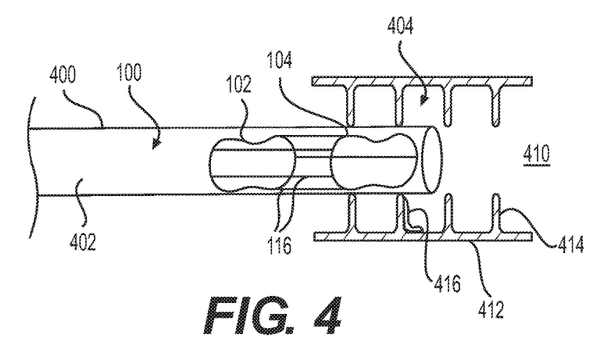
FIGS. 4-6 are in vivo illustrations of a method of inserting the tissue expander of FIG. 1 into a body lumen.
Figure 5:
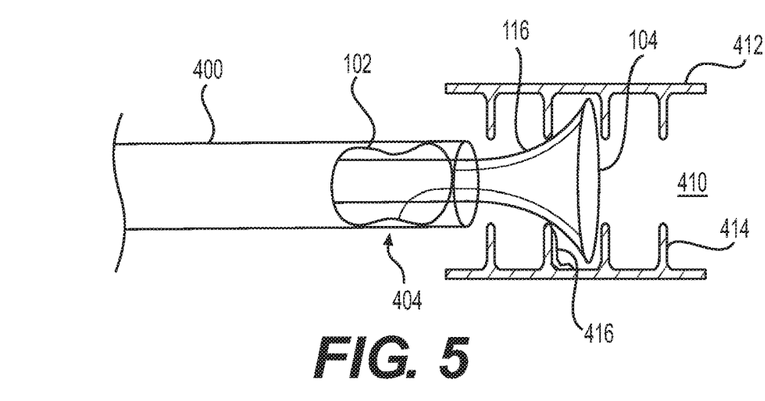

Tissue expander 100 may be movable from a collapsed configuration shown in FIG. 4 to a partially-collapsed, partially-expanded configuration shown in FIG. 5, to an expanded configuration shown in FIGS. 1 and 6.

Referring to FIG. 4, tissue expander 100 may be inserted into a lumen 402 of an elongate member 400. Elongate member 400 may be flexible in order to navigate tortuous anatomy within a patient, and may extend from a proximal end (not shown) toward a distal end 404. In some examples, elongate member 400 may be uniformly flexible, or may include portions having varied flexibility. For example, distal end 404 of elongate member 400 may be more flexible than the proximal end of elongate member 400. Elongate member 400 may include any suitable dimensions as is known in the art, and may be used in place of or in combination with any traditional medical scope, such as, e.g., an endoscope, a ureteroscope, a colonoscope, a hysteroscope, a uteroscope, a bronchoscope, or a cystoscope. Elongate member 400 may be directly inserted into the body of a patient or may be extended over a guidewire using one or more lumens. Elongate member 400 also may be inserted into a laparoscopic port, a single incision port, an over-tube, a bouché, or any other suitable member.

Tissue expander 100 may be delivered to a body lumen 410 by elongate member 400 or by another suitable delivery system. Body lumen 410 may be a lumen of the colon, although other suitable body lumens are also contemplated. Body lumen 410 may be defined by a tissue wall 412, which may include an irregular topology or surface represented in the Figures by a plurality of longitudinally spaced ridges 414 (or other irregularities in tissue) that may extend radially inward from an inner circumference of the tissue wall 412 into the body lumen 410.

Distal end 404 may be positioned distally of target tissue 416 (which may be cancerous or potentially-cancerous tissue desired to be resected) as shown in FIG. 4. The second support 104 then may be deployed from distal end 404 and may expand automatically (e.g., self-expand) or may be expanded by a suitable mechanism as set forth above (FIG. 5). The distal end 404 of elongate member 400 then may be retracted proximally or otherwise positioned proximal to target tissue 416, at which point first support 102 may be deployed from distal end 404. Once first support 102 is deployed from distal end 404, first support 102 may expand radially to engage the tissue wall 412 proximally of target tissue 416, and spacers 116 also may urge toward their expanded configurations. First support 102 and second support 104 may engage the inner surface of tissue wall 412, and thus, when spacers 116 longitudinally expand, the portion of tissue wall 412 disposed between first support 102 and second support 104 may be spread out to create a substantially uniform, cylindrical surface (as shown in FIG. 6), so as to cause tissue irregularities, like ridges 414, to stretch and flatten.

First support 102 and second support 104 may be coupled to one another by flexible spacers 116 while disposed within elongate member 400. However, in other examples, first support 102 and second support 104 may be uncoupled to one another while disposed within elongate member 400, and may be inserted separately into the body lumen 410. In such examples, a user may position second support 104 distally of target tissue 416, and subsequently position first support 102 proximally of target tissue 416. Once first support 102 and second support 104 are expanded by the mechanisms set forth above, one or more spacers 116 may be inserted between first support 102 and second support 104. Spacers 116 then may be expanded until a desired distance is achieved between first support 102 and second support 104, which may be when, for example, the surface of tissue wall 412 becomes substantially cylindrical, or when first support 102 and second support 104 are separated from each other by a distance approximately equal to the length of the removal tool 300 between attachment portions 308.

Figure 7:
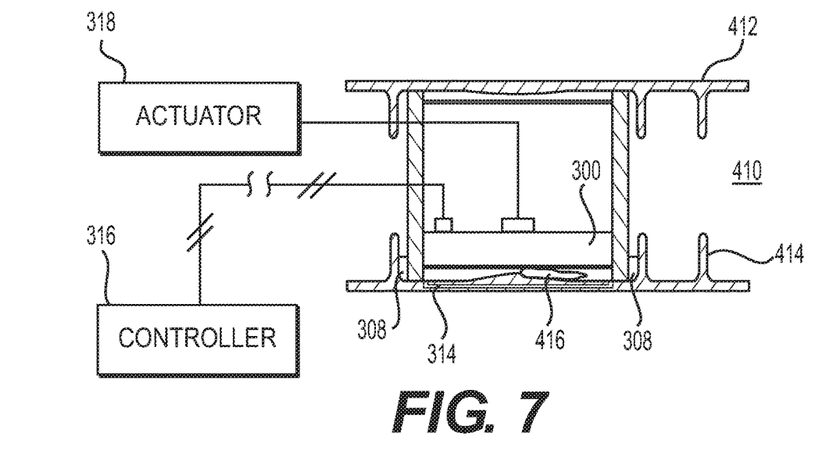
FIG. 7 is an in vivo illustration of the tissue expander of FIG. 1 and the removal tool of FIG. 3 within a body lumen.

Once the first support 102 and second support 104 are spaced apart from one another by a desired distance (that, e.g., corresponds to the distance between attachment portions 308), removal tool 300 may be inserted into body lumen 410 via, e.g., elongate member 400 or another suitable delivery member, and may be coupled with first support 102 and second support 104 as shown in FIG. 7. In order to couple removal tool 300 to first support 102 and second support 104, the mating features 312 of removal tool 300 may be aligned with the corresponding mating features 110 of first support 102 and second support 104. Once secured to first support 102 and second support 104, a depth of cutting member 314 may be set manually by the user or by controller 316 prior to positioning it over the target tissue 416. Controller 316 may be a rotating rod extending the entire width of the tool, and may have teeth that engage with the cutting member 314 inside the tool. The rod could be rotated on either side of the tool to adjust the depth of the cutting member 314. The depth of the cutting member 314 may be set ex vivo based on diagnostic information available to the operator but could also be actuated in vivo. The controller 316 may also be a screw or plunger that applies force from the top of the tool. Counter-force may be applied by a spring or other mechanism inside the tool that would tend to reduce the cutting depth. By increased the force from the top, the cutting depth may be increased. Controller 316 may be manually actuated or could be actuated by a piezoelectric motor controlled by an ex vivo driver. Removal tool 300 then may be actuated by actuator 300 along a circumferential path defined by the circumferences of first support 102 and second support 104, removing tissue from tissue wall 412, including target tissue 416, via cutting member 314.

In some examples, one or more of spacers 116 may be removed or repositioned before cutting member 314 is used to remove tissue from tissue wall 412. That is, because removal tool 300 and cutting member 314 travel circumferentially about the body lumen via first support 102 and second support 104, the presence of spacers 116 along the circumference of the first support 102 and second support 104 may interfere with the removal of target tissue by blocking the path of removal tool 300 along the track provided by mating features 110. In some examples, all of spacers 116 may be removed from the body lumen 410 before or after removal tool 300 is positioned into the body lumen 410. In one example, all of the spacers 116 may be removed, and first support 102 and second support 104 may be configured to retain their position relative to one another by one or more surface features or anchoring features 118. In another example, only those spacers 116 necessary to clear a circumferential path for removal tool 300 may be removed. Spacers 116 also may be repositioned to create a circumferential path for removal tool 300 around body lumen 410. That is, spacers 116 may be configured to be moved along a circumferential path created by first support 102 and second support 104. In such examples, spacers 116 may be slid along a track of mating feature 110 from a first circumferential position to a second circumferential position if access of the removal tool 300 to the targeted tissue 416 is blocked when a spacer 116 is disposed in the first circumferential position.

The en bloc resected tissue may be removed from body lumen 410 by conventional mechanisms, such as, e.g., graspers, suction, or the like. Bleeding may be controlled using conventional methods after the resection is complete. The removal tool 300 then may be removed, followed by first support 102, second support 104, and spacers 116 (if not already removed).

In at least some examples of the present disclosure, the need to visualize a cut and submucosa during the procedure may be eliminated because the cut depth may be controlled by the cutting member 314. The need to inject saline or similar solutions to raise the target tissue or tumor also may be eliminated. In some examples of the present disclosure, this may result in fewer or no through-the-scope device exchanges being performed. The risk of damage to the muscularis also may be reduced because of the increased control of the cutting depth.

Figure 8:
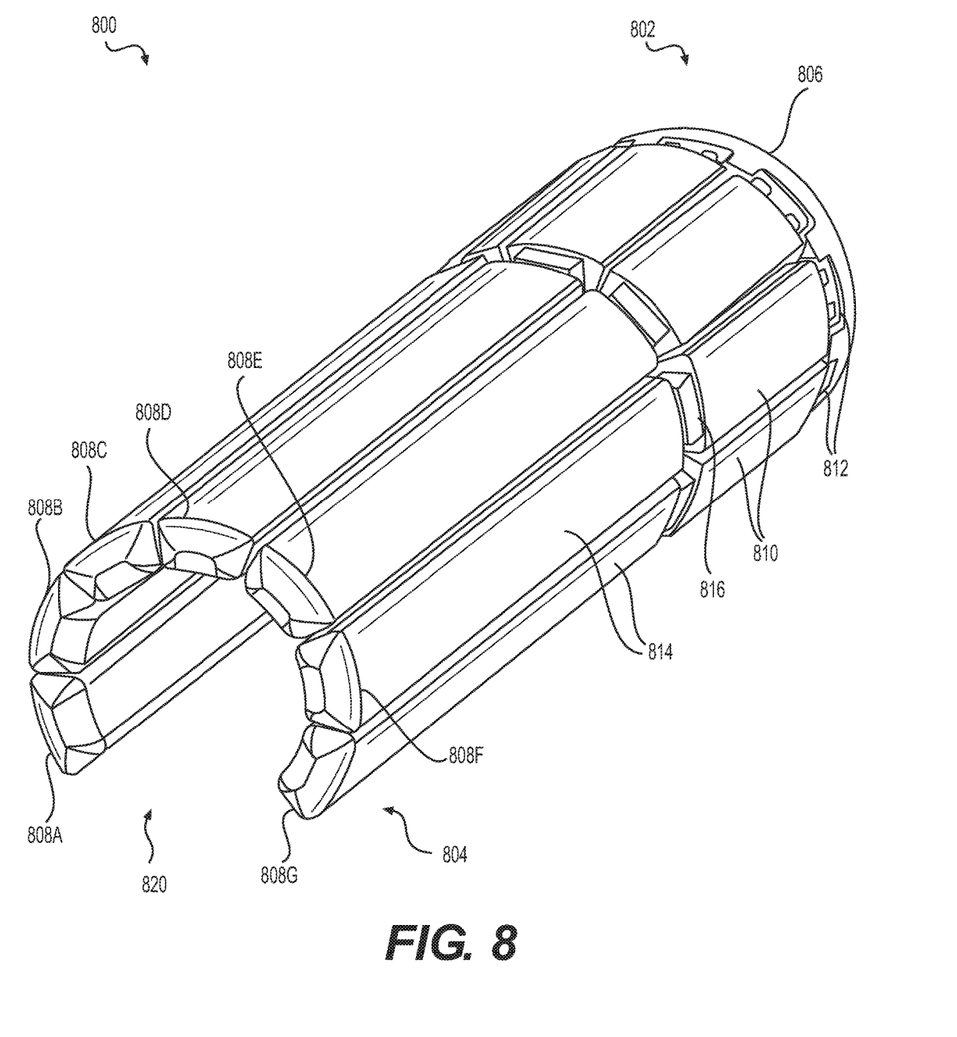
FIG. 8 is a perspective view of a tissue expander in a collapsed configuration according to another example of the present disclosure.
Figure 9:
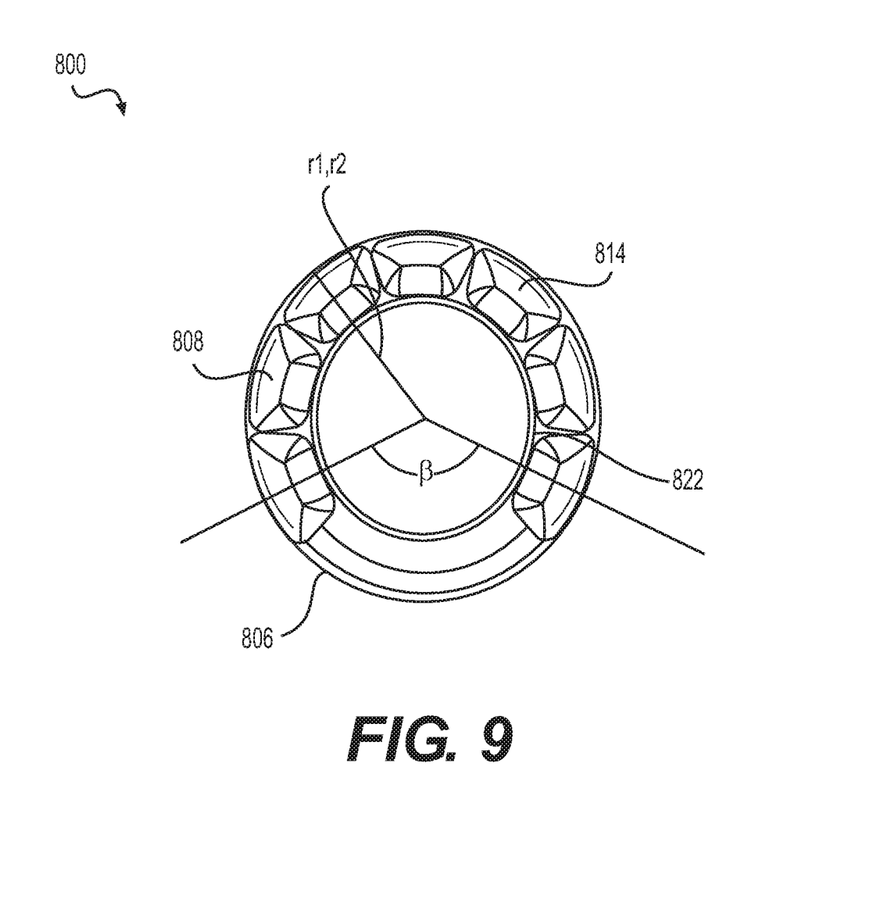
FIG. 9 is an end view of the tissue expander of FIG. 8 in the collapsed configuration.
Figure 10:
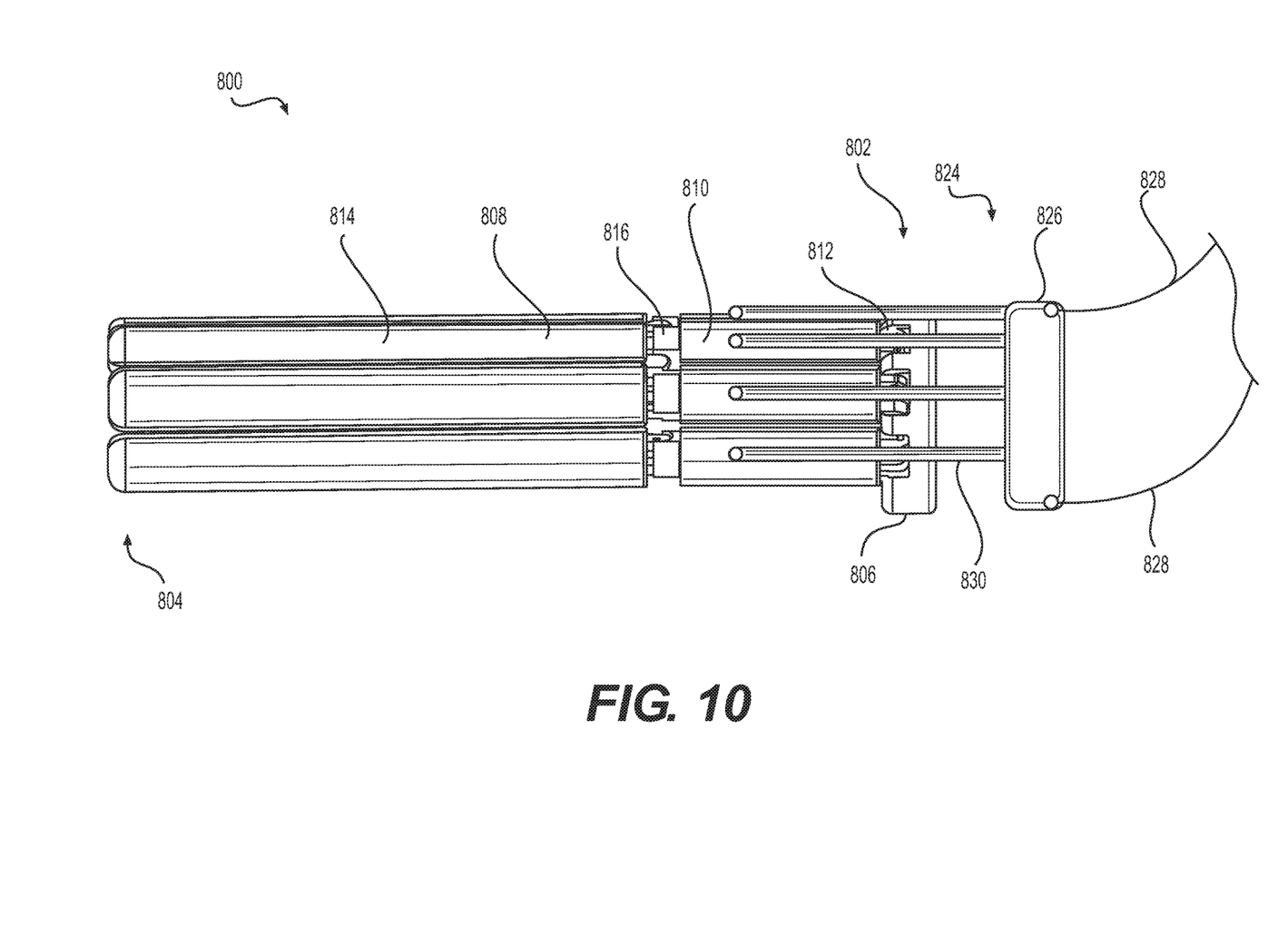
FIG. 10 is a side view of the tissue expander of FIG. 8 in the collapsed configuration.
Figure 11:
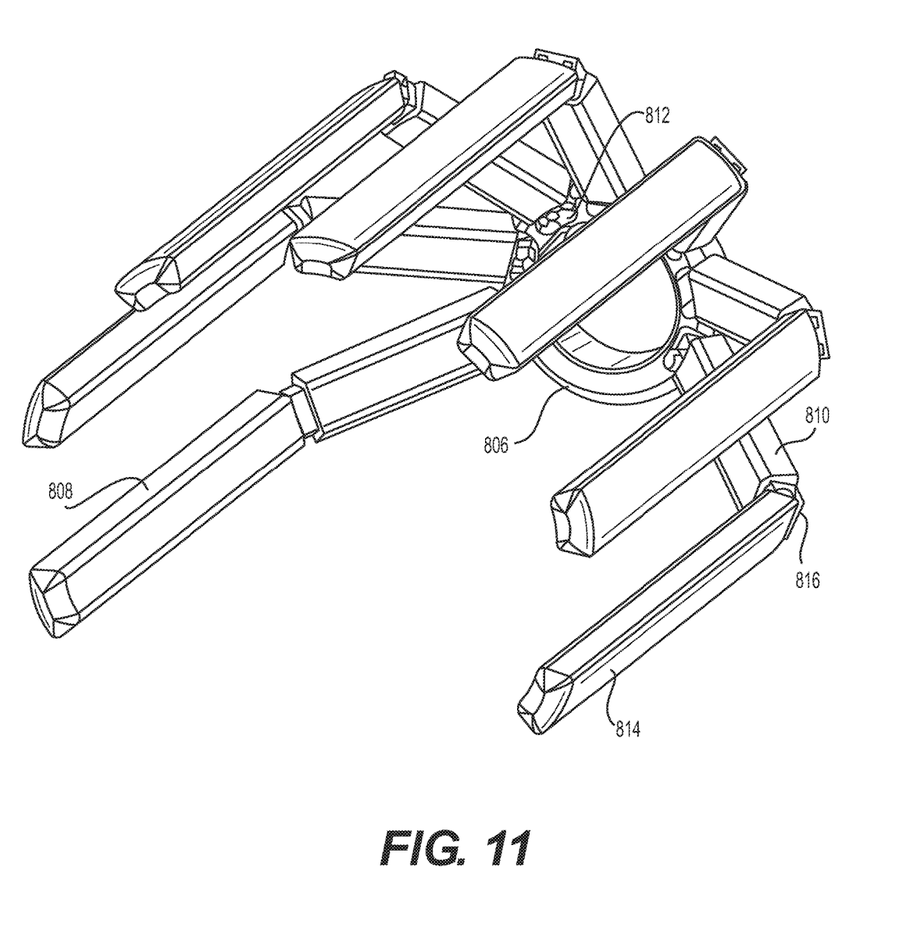
FIG. 11 is a perspective view of the tissue expander of FIG. 8 in an expanded configuration.
Figure 12:
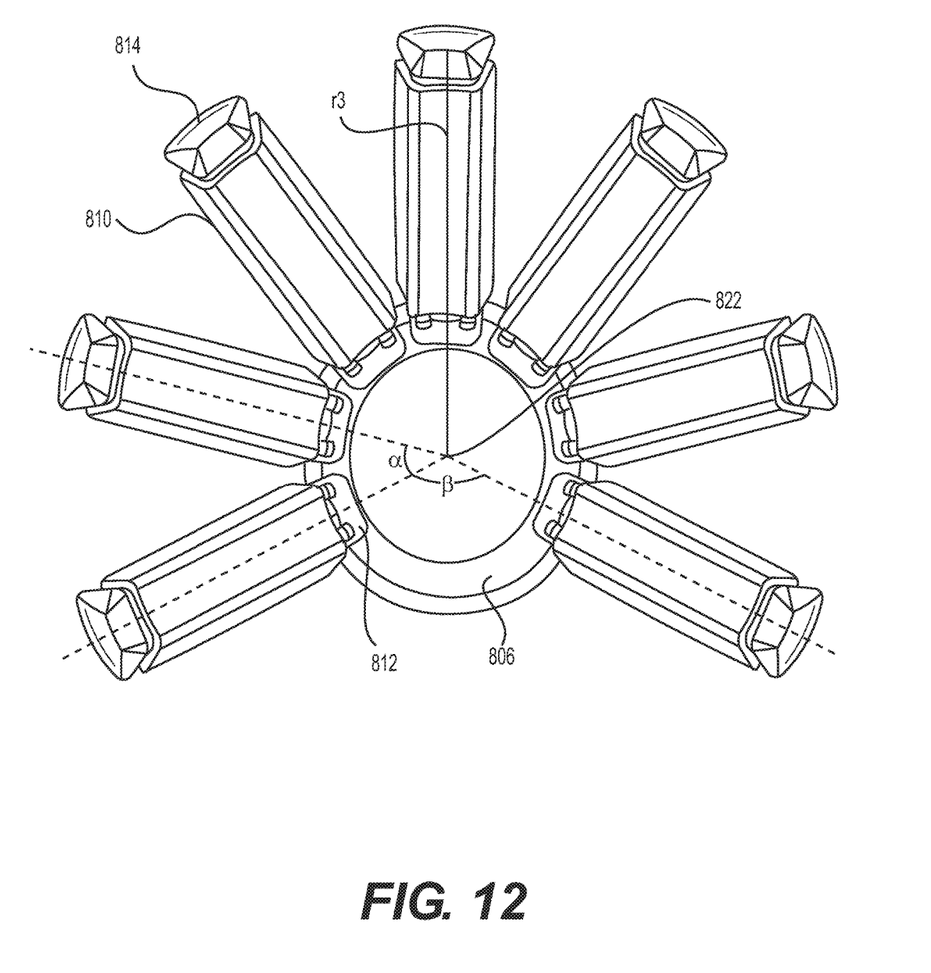
FIG. 12 is an end view of the tissue expander of FIG. 8 in the expanded configuration.
Figure 13:
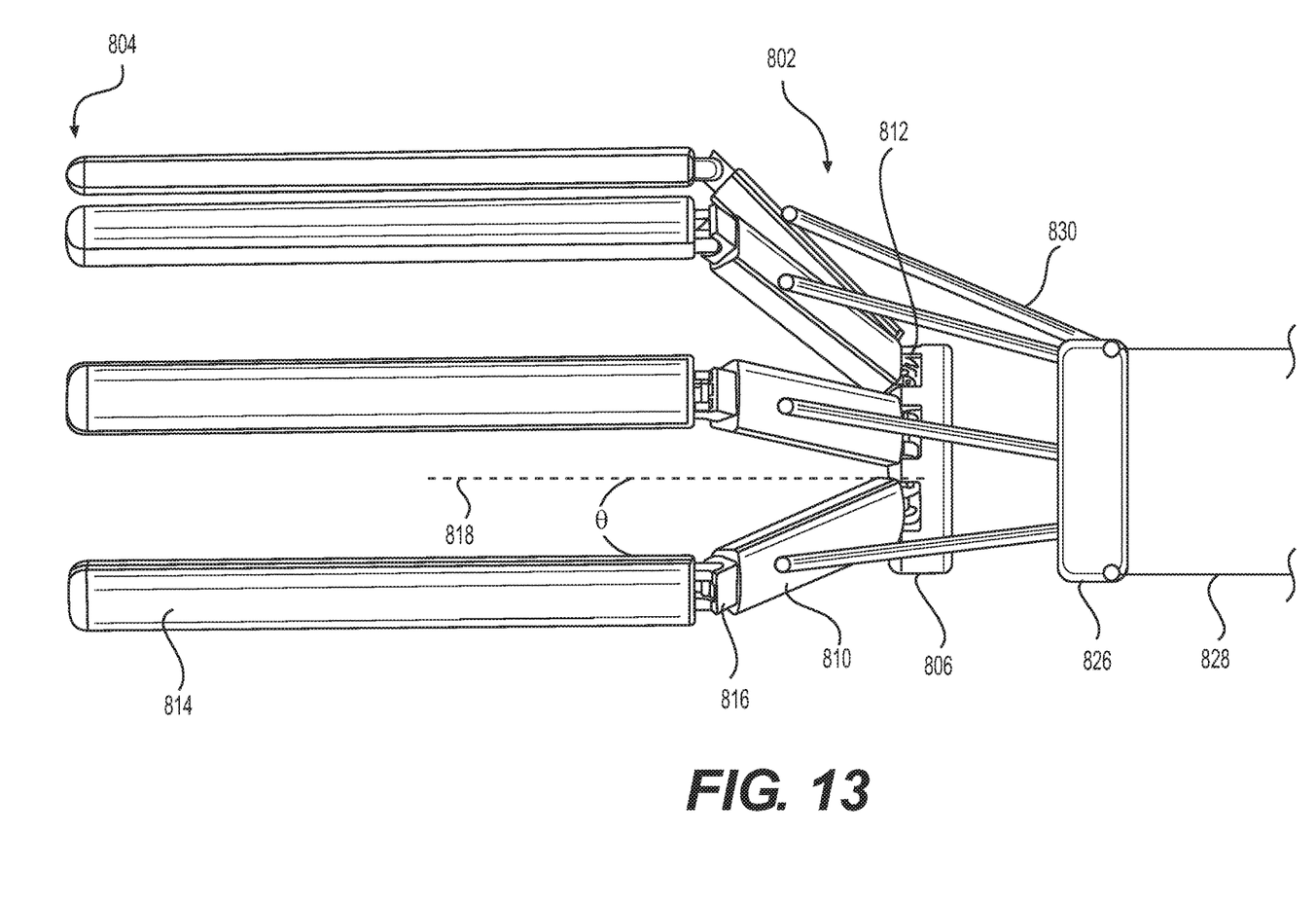
FIG. 13 is a side view of the tissue expander of FIG. 8 in the expanded configuration.

A tissue expander 800 is shown in FIGS. 8-10 in a collapsed configuration, and in FIGS. 11-13 in an expanded configuration. The tissue expander 800 may be movable between the collapsed configuration and the expanded configuration as set forth in further detail below. The tissue expander may extend from a proximal end 802 toward a distal end 804. The tissue expander 800 may include a support 806, which may be a ring having a circular or other suitable cross-section.

A plurality of leg assemblies 808 may extend distally from the support 806. Seven leg assemblies 808a-g are shown in the example of FIG. 8, but additional or fewer leg assemblies 808 may be utilized. Each leg assembly 808 may include a first leg 810 coupled to the support 806 at a joint 812. Each leg assembly 808 further includes a second leg 814 extending distally from first leg 810 at a joint 816. The first legs 810 and second legs 814 may have any suitable length, such as, e.g., 1.0 cm and 4.0 cm respectively, although other suitable dimensions are also contemplated. In some examples, second legs 814 may be approximately 1.5 to 10.0 times longer than first legs 810, although other suitable ratios are also contemplated. First legs 810 and second legs 814 may be formed of any suitable biocompatible material including, but not limited to metals, alloys, plastics, or the like, and may include adhesive, bioadhesive, antibiotic, or other coatings. In some examples, the surfaces of first legs 810 and second legs 814 may include one or more anchoring features similar to anchoring features 118 described above, or may be roughened, notched, slotted, etched, sand-blasted, coated or otherwise modified to provide a better gripping surface and attachment to tissue walls surrounding a body lumen.

Joints 812 and 816 may be pivotable joints such as, e.g., a ball and socket joint, a pivot joint, a swivel joint, or another suitable pivotable joint. Joint 812 may include a locking mechanism configured to limit the proximal retraction of first legs 810. In some examples, the locking mechanism of joint 812 may prevent the first legs 810 from being retracted proximally of support 806. While first leg 810 is in the expanded configuration, an angle Θ (shown in perspective in FIG. 13) may be measured between a longitudinal axis 818 of tissue expander 800 and first leg 810, and may be limited to 45 degrees or fewer. However, other suitable configuration are also contemplated, including examples where the angle Θ is from 15 degrees to 90 degrees. Joint 816 also may include a locking mechanism that is configured to maintain second leg 814 substantially parallel to a longitudinal axis of the tissue expander 800 in both the collapsed configuration and the expanded configuration.

In the collapsed configuration, the entirety of each leg assembly 808 may be substantially parallel to a central longitudinal axis 822 of the tissue expander 100. That is, the first leg 810 and the second leg 814 of each leg assembly 808 may be substantially parallel to the central longitudinal axis 822 of tissue expander 800 while in the collapsed configuration. As seen in FIGS. 8 and 9, most pairs of adjacent leg assemblies 808a-g may be in contact with one another, or may be separated from one another by a small distance. However, at least one pair of adjacent leg assemblies (e.g., adjacent leg assemblies 818a and 818g) may be separated from one another by a gap 820 in the collapsed configuration. In examples where there is some space or a gap between the other adjacent leg assemblies 808, the length of gap 820 may be substantially larger than those other gaps. In some examples, gap 820 may be 1.5 to 1000 times larger than the gaps separating other adjacent leg assemblies, although other suitable ratios and proportions are also contemplated. Referring to FIG. 9, in the collapsed configuration, a radius r1 from the central longitudinal axis 822 of tissue expander 800 to the outer circumference of leg assemblies 808 may be substantially similar to a radius r2 from the central longitudinal axis 822 to the outer circumference of support 806. In some examples, r1 and r2 may be 1.27 cm, while in other examples, r1 and r2 may be any suitable dimension such as, e.g., 0.1 cm to 10.0 cm. In some examples, the gap 820 may be positioned adjacent to target tissue that will be resected. Once the tissue expander 800 is transitioned to the expanded configuration, the adjacent tissue may be substantially flattened to facilitate resection.

Referring to FIGS. 10 and 13, tissue expander 800 may include an actuating mechanism 824 configured to reciprocally move tissue expander 800 between the collapsed configuration and the expanded configuration. Actuating mechanism 824 may include a support 826, which, like support 806 may be a ring support having a central lumen disposed therethrough. The support 826 may be coupled to one or more actuating members 828, such as, e.g., wires or the like configured to move support 826 from a first position shown in FIG. 10 to a second position shown in FIG. 13. The support 806 and the support 826 each may include a lumen, and those lumens may be collinear to enable the passage of an endoscope through the lumens. Support 806 and support 826 may separate form one another when moving from the collapsed configuration of FIG. 10 to the expanded configuration of FIG. 13. In some examples, both support 806 and support 826 may be positioned or slid over an endoscope. One or more linkages 830 (e.g., rigid cables or struts) may extend distally from support 826 and may be coupled to an outer circumferential surface of each first leg 810 of tissue expander 800. When a proximal force or tension is applied to the actuating members 828, support 826 and linkages 830 may move proximally (while support 806 remains stationary), pulling leg assemblies 808 proximally to expand tissue expander 800 into the expanded configuration shown in FIGS. 11-13. The proximal force may be released from actuating members 828 to cause tissue expander 800 to revert back to the collapsed configuration shown in FIG. 10. Tissue expander 800 may be biased to collapsed configuration or to the expanded configuration.

In the expanded configuration, each first leg 810 may be radially offset from center longitudinal axis 822 by 15 degrees to 90 degrees, and each first leg 810 may be offset form center longitudinal axis 822 by the same amount as every other first leg 810. Because each first leg 810 may be radially offset from the central longitudinal axis 822 at an angle Θ, the distance between central longitudinal axis 822 and leg 810 may increase linearly in the distal direction while tissue expander 800 is in the expanded configuration.

Referring to FIG. 12, in the expanded configuration, most adjacent leg assemblies 808 may be spaced from one another by a first angle α, such as, e.g., 10 to 60 degrees, while at least one other pair of adjacent leg assemblies 808 may be spaced apart from one another by a second angle β that is greater than angle α, such as, e.g., 90 to 180 degrees. In one example, angle α may be 43.3 degrees and angle β may be 100 degrees. The angles α and β may be defined in a plane that is normal to central longitudinal axis 822. Second legs 814 may be disposed at a radius r3 from central longitudinal axis 822 in the expanded configuration. Radius r3 may be 1.5 to 5.0 times larger than radii r1 and r2, although other suitable ratios and proportions are also contemplated. Radius r3 may be 5.0 cm, or may be another suitable dimension, such as, e.g., 1.5 cm to 25 cm. The angle β may be substantially similar in both the collapsed configuration and the expanded configuration. In the expanded configuration, second legs 814 may be unconnected and unattached to one another. That is, second legs 814 may have free distal ends in the expanded configuration.

The tissue expander 800 may be positioned at a distal end of a scope via, e.g., support 806. Once the tissue expander 800 is in the expanded configuration, an operator may detach the tissue expander 800 from the scope, allowing the scope to move freely within the body lumen to, e.g., perform the cutting or other functions necessary for a resection. This arrangement may improve the visibility and use of tools through the working channel of the scope. The tissue expander 800 may remain tethered to the scope to allow for easy removal of both the scope and the tissue expander 800 once the procedure is completed.

In an alternative example, one or more of first leg 810 and second leg 814 may be formed of a shape memory material, such as, e.g., nitinol. In this alternative example, joints 812 and 816 may not be pivotable joints, but may instead be bends in a continuous piece of the shape memory material. In this example, the tissue expander 800 may be pre-bent into the expanded configuration as shown in FIGS. 11-13, and may be constrained by a sheath (e.g., elongate member 400) in order to be maintained in the collapsed configuration. When the elongate member is positioned at the appropriate location in a body lumen, a pusher may be used to apply a distal force to the proximal end of the tissue expander 800 to deploy the tissue expander 800 from the elongate member. After completion of the procedure, the pusher member may be retracted, and the tissue expander 800 can be retracted within a lumen of the elongate member.

Tissue expander 800 may be positioned in a body lumen of a patient while disposed in the collapsed configuration, and while support 806 is attached to the distal end of an endoscope. Once a target area desired to be resected is identified, the scope and tissue expander 800 may be manipulated to place gap 820 adjacent to the target area. Once gap 820 is adjacent the target area, a proximal force may be applied to actuating members 828, causing support 826 to retract proximally relative to support 806. This may cause the first legs 810 of the plurality of leg assemblies 808 to pivot proximally, which in turn may cause the tissue expander 800 to move from the collapsed configuration of FIGS. 8-10 to the expanded configuration of FIGS. 11-13. The positioning of gap 820 adjacent the target area may cause the tissue disposed in the target area to substantially flatten when tissue expander 800 is in the expanded configuration. The relatively large distance between adjacent leg assemblies 808a and 808g that define gap 820 (referring to FIG. 8) relative to other adjacent leg assemblies may create a relatively large flattened surface for a surgeon or user to operate on. A resection tool (e.g., cutter, snare, or the like) may be passed through a scope to remove tissue from the flattened surface between adjacent leg assemblies 808a and 808g. When the resection is completed, the proximal force on actuating members 828 may be released causing tissue expander 800 to revert to the collapsed configuration. If tissue expander 800 was previously separated from the scope, it may be reattached, and both the scope and tissue expander 800 may be removed from the body.

As used herein, two objects and/or references (e.g., axes, planes, or the like) may be "substantially parallel" to one another if they are parallel to one another, are offset from one another by less than 1 degree, by less than 5 degrees, or by less than 10 degrees, as dictated by, e.g., machining imperfections and the like.

Those skilled in the art will understand that the medical devices set out above can be implemented in any suitable body lumen (e.g., blood vessels, the biliary tract, urological tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other examples of the present disclosure will be apparent to those skilled in the art from consideration of the specification and practice of the examples disclosed herein. It is intended that the specification and examples be considered as exemplary only, and departures in form and detail may be made without departing from the scope and spirit of the present disclosure as defined by the following claims.

What is claimed is:

1. A device for treating tissue, comprising:
   a tissue expander configured to be inserted into a body lumen and stretch tissue surrounding the body lumen; and
   a tool configured to be coupled to the tissue expander and move along a path defined by the tissue expander, wherein the tissue expander includes a first support ring and a second support ring, wherein the path is defined at a first end by the first support ring and at a second end by the second support ring, and wherein the tool is configured to move relative to the first support ring and the second support ring along the path.

2. The device of claim 1, wherein the tool is configured to move circumferentially along the path.

3. The device of claim 2, further including one or more spacers disposed between the first support ring and the second support ring, wherein the one or more spacers are longitudinally expandable.

4. The device of claim 3, wherein the tool includes a first attachment portion configured to be coupled to the first support ring, and a second attachment portion configured to be coupled to the second support ring, wherein a length of the tool between the first attachment portion and the second attachment portion is equal to a length of the one or more spacers.

5. The device of claim 4, wherein the first attachment portion includes a first mating feature, the second attachment portion includes a first mating feature, the first support ring includes a second mating feature disposed on at least one of a proximally-facing surface or a distally-facing surface of the first support ring, and the second support ring includes a second mating feature disposed on at least one of a proximally-facing surface or a distally-facing surface of the second support ring, wherein the first mating feature of the first attachment portion is complementary to the second mating feature of the first support ring, and wherein the first mating feature of the second attachment portion is complementary to the second mating feature of the second support ring.

6. The device of claim 5, wherein one of the first mating feature or the second mating feature is a recess, and wherein the other of the first mating feature or the second mating feature is a pin, bearing, ball, protrusion, wheel, or roller configured to be received by the recess.

7. The device of claim 1, wherein the tool includes a cutting member extending radially outward when the tool is coupled to the tissue expander.

8. The device of claim 1, wherein the tissue expander includes anchoring features extending radially outward from an outer circumferential surface.

9. The device of claim 3, wherein the one or more spacers include a shape memory material that is set or pre-shaped into a straight expanded configuration.

10. The device of claim 3, wherein the one or more spacers are removable from the first support ring and the second support ring.

11. The device of claim 7, wherein the cutting member is a knife, a blade, or an edge.

12. The device of claim 1, wherein the tool is movable in a first circumferential direction around the tissue expander, and is movable in a second circumferential direction, opposite of the first circumferential direction, around the tissue expander.

13. The device of claim 1, wherein the first support ring and the second support ring each includes a shape memory material.

14. The device of claim 1, wherein the tissue expander is movable between a collapsed configuration and an expanded configuration, and the tissue expander is biased into the expanded configuration such that when a constraining force is removed from the tissue expander, the tissue expander urges itself to the expanded configuration.

15. The device of claim 8, wherein the anchoring features are bioabsorbable.

16. The device of claim 8, wherein the anchoring features are removable from the tissue expander by a frangible link.

17. A device for treating tissue, comprising:
   a tissue expander configured to be inserted into a body lumen and stretch tissue surrounding the body lumen, wherein the tissue expander includes:
      a first support ring including a first mating feature disposed on at least one of a proximally-facing surface or a distally-facing surface of the first support ring; and
      a second support ring including a first mating feature disposed on at least one of a proximally-facing surface or a distally-facing surface of the second support ring;
   a tool configured to be coupled to the tissue expander and move along a path defined by the tissue expander; wherein:
      the path is defined at a first end by the first support ring and at a second end by the second support ring;
      the tool is configured to move circumferentially along the path;
      the tool includes a first attachment portion configured to be coupled to the first support ring, the first attachment portion including a second mating feature that is complementary to the first mating feature of the first support ring; and
      the tool includes a second attachment portion configured to be coupled to the second support ring, the second attachment portion including a second mating feature that is complementary to the first mating feature of the second support ring;
   one or more spacers disposed between the first support ring and the second support ring, wherein:
      the one or more spacers are longitudinally expandable; and a length of the tool between the first attachment portion and the second attachment portion is equal to a length of the one or more spacers.

18. The device of claim 17, wherein the tool includes a cutting member extending radially outward when the tool is coupled to the tissue expander.

19. A device for treating tissue, comprising:
- a tissue expander configured to be inserted into a body lumen and stretch tissue surrounding the body lumen, wherein the tissue expander includes:
  - a first support ring, wherein the first support ring includes a first mating feature disposed on at least one of a proximally-facing surface or a distally-facing surface of the first support ring; and
  - a second support ring, wherein the second support ring includes a first mating feature disposed on at least one of a proximally-facing surface or a distally-facing surface of the second support ring; and
- a tool configured to be coupled to the tissue expander and move along a path defined by the tissue expander, wherein the tool includes:
  - a first attachment portion configured to be coupled to the first support ring, the first attachment portion including a second mating feature that is complementary to the first mating feature of the first support ring, and
  - a second attachment portion configured to be coupled to the second support ring, the second attachment portion including a second mating feature that is complementary to the first mating feature of the second support ring.

20. The device of claim 19, wherein the tool includes a cutting member extending radially outward when the tool is coupled to the tissue expander.

* * * * *